(12) United States Patent
Vale

(10) Patent No.: US 11,076,876 B2
(45) Date of Patent: *Aug. 3, 2021

(54) SYSTEM FOR REMOVING A CLOT FROM A BLOOD VESSEL

(71) Applicant: NEURAVI LIMITED, Galway (IE)

(72) Inventor: David Vale, County Galway (IE)

(73) Assignee: NEURAVI LIMITED, Galway (IE)

( * ) Notice: Subject to any disclaimer, the term of this patent is extended or adjusted under 35 U.S.C. 154(b) by 118 days.

This patent is subject to a terminal disclaimer.

(21) Appl. No.: 16/294,661

(22) Filed: Mar. 6, 2019

(65) Prior Publication Data

US 2019/0201014 A1  Jul. 4, 2019

Related U.S. Application Data

(63) Continuation of application No. 14/698,552, filed on Apr. 28, 2015, now Pat. No. 10,265,086.

(Continued)

(51) Int. Cl.
*A61B 17/221* (2006.01)
*A61F 2/01* (2006.01)
*A61B 17/22* (2006.01)

(52) U.S. Cl.
CPC ............ *A61B 17/221* (2013.01); *A61F 2/013* (2013.01); *A61B 2017/2212* (2013.01);
(Continued)

(58) Field of Classification Search
CPC .......... A61B 17/32056; A61B 17/3207; A61B 17/320716; A61B 17/320741;
(Continued)

(56) References Cited

U.S. PATENT DOCUMENTS 4,243,040 A   1/1981   Beecher
4,324,262 A   4/1982   Hall
(Continued)

FOREIGN PATENT DOCUMENTS

CN   103071195 A   5/2013
CN   105726163 A   7/2016
(Continued)

OTHER PUBLICATIONS

US 6,348,062 B1, 02/2002, Hopkins (withdrawn)
(Continued)

*Primary Examiner* — Mohamed G Gabr
(74) *Attorney, Agent, or Firm* — Troutman Pepper Hamilton Sanders LLP

(57) ABSTRACT

A system for removing an obstruction from a blood vessel. The system can include a catheter with a proximal section with a proximal section lumen diameter, a distal section with a distal section lumen diameter less than the proximal section lumen diameter, an intermediate section extended between proximal and distal sections. The system can include a clot retrieval device with a clot engaging element. The system can include a shaft being advanceable through the lumen of the catheter the obstruction of the blood vessel, the shaft can include a shaft proximal section; a shaft distal section attached to the clot engaging element and configured to cross the obstruction, a diameter of the shaft proximal section being greater than a diameter of the shaft distal section thereby inhibiting the shaft proximal section from distally advancing through the catheter distal section.

17 Claims, 6 Drawing Sheets

Related U.S. Application Data

(60) Provisional application No. 62/019,137, filed on Jun. 30, 2014.

(52) U.S. Cl.
CPC ............ *A61B 2017/22034* (2013.01); *A61B 2017/22079* (2013.01); *A61F 2002/016* (2013.01)

(58) Field of Classification Search
CPC .......... A61B 17/320758; A61B 17/221; A61B 17/22031; A61B 17/22; A61B 17/22032; A61B 2017/2212; A61B 2017/22034; A61B 2017/00867; A61B 2017/22035; A61B 2017/2215; A61B 2017/2217; A61B 2017/22067; A61B 2017/22079; A61B 2017/22084; A61B 2017/22042; A61B 2017/22038; A61B 2017/22044; A61F 2/013; A61F 2/95; A61F 2/01; A61F 2230/0006; A61F 2230/0008; A61F 2230/001; A61F 2230/005; A61F 2230/0058; A61F 2230/08; A61F 2002/011; A61F 2002/018; A61F 2002/016; A61M 2025/0042; A61M 2025/0681; A61M 25/104
USPC ........................................................ 606/200
See application file for complete search history.

(56) References Cited

U.S. PATENT DOCUMENTS

| | | |
|---|---|---|
| 4,575,371 A | 3/1986 | Nordqvist et al. |
| 4,738,666 A | 4/1988 | Fuqua |
| 4,767,404 A | 8/1988 | Renton |
| 4,793,348 A | 12/1988 | Palmaz |
| 4,873,978 A | 10/1989 | Ginburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus ................. A61M 25/104 604/913 |
| 5,385,562 A | 1/1995 | Adams et al. |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu et al. |
| 5,538,512 A | 7/1996 | Zenzon et al. |
| 5,549,626 A | 8/1996 | Miller et al. |
| 5,558,652 A | 9/1996 | Henke |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut et al. |
| 5,695,519 A | 12/1997 | Summers et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Daniels et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,063,113 A | 5/2000 | Kavteladze et al. |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz ................. A61B 17/12022 606/1 |
| 6,106,548 A | 8/2000 | Roubin et al. |
| 6,129,739 A | 10/2000 | Khosravi |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard et al. |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,346,116 B1 | 2/2002 | Brooks et al. |
| 6,348,056 B1 | 2/2002 | Bates |
| 6,350,271 B1 | 2/2002 | Kurz et al. |
| 6,361,545 B1 | 3/2002 | Macoviak et al. |
| 6,375,668 B1 | 4/2002 | Gifford et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. et al. |
| 6,530,935 B2 | 3/2003 | Wensel |
| 6,530,939 B1 | 3/2003 | Hopkins |
| 6,540,768 B1 | 4/2003 | Diaz |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |

(56) References Cited

U.S. PATENT DOCUMENTS

| | | |
|---|---|---|
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome et al. |
| 6,730,104 B1 | 5/2004 | Sepetka |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 6,997,939 B2 | 2/2006 | Linder et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel et al. |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Clubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne et al. |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,713 B2 | 11/2013 | Ferrera et al. |
| 8,608,761 B2 | 12/2013 | Osborne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Martin et al. |
| 8,795,317 B2 | 8/2014 | Martin et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolik et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |

(56) References Cited

U.S. PATENT DOCUMENTS

| | | |
|---|---|---|
| 9,198,687 B2 | 12/2015 | Fulkerson et al. |
| 9,204,887 B2 | 12/2015 | Cully et al. |
| 9,221,132 B2 | 12/2015 | Imamura et al. |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 * | 4/2019 | Vale ............ A61B 17/221 |
| 10,716,915 B2 | 7/2020 | Ogle et al. |
| 10,610,668 B2 | 8/2020 | Burkholz et al. |
| 2001/0001315 A1 | 5/2001 | Bates |
| 2001/0016755 A1 | 8/2001 | Addis |
| 2001/0041899 A1 | 11/2001 | Foster |
| 2001/0044598 A1 | 11/2001 | Parodi |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter et al. |
| 2002/0052620 A1 | 5/2002 | Barbut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0125798 A1 | 7/2003 | Martin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0176884 A1 | 9/2003 | Berrada et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0236533 A1 | 12/2003 | Wilson |
| 2004/0010280 A1 | 1/2004 | Adams et al. |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153118 A1 | 8/2004 | Clubb |
| 2004/0193107 A1 | 9/2004 | Pierpont et al. |
| 2004/0260333 A1 | 12/2004 | Dubrul et al. |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0125024 A1 | 6/2005 | Sepetka |
| 2005/0171566 A1 | 8/2005 | Kanamaru |
| 2005/0187570 A1 | 8/2005 | Nguyen et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0267491 A1 | 12/2005 | Kellett et al. |
| 2005/0288686 A1 | 12/2005 | Sepetka |
| 2006/0009785 A1 | 1/2006 | Maitland et al. |
| 2006/0009799 A1 | 1/2006 | Kleshinski et al. |
| 2006/0030933 A1 | 2/2006 | DeLeggge et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0106361 A1 | 5/2006 | Muni et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |

(56) References Cited

U.S. PATENT DOCUMENTS

| | | |
|---|---|---|
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin ............ A61B 17/22012 606/200 |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello ............ A61B 17/221 606/159 |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay ............ A61M 37/0069 604/511 |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson ............ A61B 17/221 604/266 |
| 2010/0030186 A1 | 2/2010 | Stivland |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1* | 11/2010 | Olsen ............ A61B 17/221 606/200 |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog ............ A61B 17/22 606/159 |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | di Palma et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera ............ A61B 17/221 606/200 |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0046359 A1 | 2/2014 | Bowman et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0183077 A1 | 7/2014 | Rosendall et al. |

(56) References Cited

U.S. PATENT DOCUMENTS

| | | |
|---|---|---|
| 2014/0188127 A1 | 7/2014 | Dubrul .................. A61B 90/39 606/127 |
| 2014/0194919 A1 | 7/2014 | Losordo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eidenschink |
| 2014/0276922 A1 | 9/2014 | McLain et al. |
| 2014/0277053 A1 | 9/2014 | Wang et al. |
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0250497 A1 | 9/2015 | Marks et al. |
| 2015/0257775 A1 | 9/2015 | Gilvarry et al. |
| 2015/0297252 A1 | 10/2015 | Miloslavski et al. |
| 2015/0313617 A1 | 11/2015 | Grandfield et al. |
| 2015/0320431 A1 | 11/2015 | Ulm, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Seifert et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0042623 A1 | 2/2018 | Batiste |
| 2018/0235743 A1 | 8/2018 | Farago et al. |
| 2019/0021759 A1 | 1/2019 | Krolik et al. |
| 2019/0046219 A1 | 2/2019 | Marchand et al. |

FOREIGN PATENT DOCUMENTS

| | | |
|---|---|---|
| CN | 106232059 A | 12/2016 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| EP | 2301450 B1 | 3/2011 |
| EP | 2628455 A1 | 8/2013 |

(56) References Cited

FOREIGN PATENT DOCUMENTS

| | | |
|---|---|---|
| GB | 2498349 A | 7/2013 |
| JP | 0919438 A1 | 1/1997 |
| WO | WO 94/24926 | 11/1994 |
| WO | WO 97/27808 | 8/1997 |
| WO | WO 97/038631 A | 10/1997 |
| WO | WO 99/20335 | 4/1999 |
| WO | WO 99/60933 | 12/1999 |
| WO | WO 99/56801 | 4/2000 |
| WO | WO 01/21077 | 3/2001 |
| WO | WO 02/02162 | 1/2002 |
| WO | WO 02/11627 | 2/2002 |
| WO | WO 02/43616 | 6/2002 |
| WO | WO 02/070061 | 9/2002 |
| WO | WO 02/094111 | 11/2002 |
| WO | WO 03/002006 | 1/2003 |
| WO | 03/018085 A2 | 3/2003 |
| WO | WO 03/030751 | 4/2003 |
| WO | WO 03/051448 | 6/2003 |
| WO | WO 2004/028571 A2 | 4/2004 |
| WO | WO 2004/056275 A1 | 7/2004 |
| WO | WO 2005/000130 A1 | 1/2005 |
| WO | WO 2005/027779 A2 | 3/2005 |
| WO | WO 2006/021407 | 3/2006 |
| WO | WO 2006/031410 | 3/2006 |
| WO | WO 2006/107641 | 10/2006 |
| WO | WO 2006/135823 A2 | 12/2006 |
| WO | WO 2007/054307 | 5/2007 |
| WO | WO 2007/068424 | 6/2007 |
| WO | WO 2008/034615 | 3/2008 |
| WO | WO 2008/051431 A1 | 5/2008 |
| WO | WO 2008/131116 | 10/2008 |
| WO | WO 2009/031338 A1 | 3/2009 |
| WO | WO 2009/076482 | 6/2009 |
| WO | WO 2009/086482 | 7/2009 |
| WO | WO 2009/103125 A1 | 8/2009 |
| WO | WO 2009/105710 A1 | 8/2009 |
| WO | WO 2010/010545 | 1/2010 |
| WO | WO 2010/046897 A1 | 4/2010 |
| WO | WO 2010/075565 A2 | 7/2010 |
| WO | WO 2010/102307 A1 | 9/2010 |
| WO | WO 2010/146581 A1 | 12/2010 |
| WO | WO 2011/013556 A1 | 2/2011 |
| WO | WO 2011/066961 A1 | 6/2011 |
| WO | WO 2011/082319 A1 | 7/2011 |
| WO | WO 2011/095352 A1 | 8/2011 |
| WO | WO 2011/106426 A1 | 9/2011 |
| WO | WO 2011/110316 A1 | 9/2011 |
| WO | WO 2012/052982 A1 | 4/2012 |
| WO | WO 2012/064726 A1 | 5/2012 |
| WO | WO 2012/081020 A1 | 6/2012 |
| WO | WO 2012/110619 A9 | 8/2012 |
| WO | WO 2012/120490 A2 | 9/2012 |
| WO | WO 2012/156924 A1 | 11/2012 |
| WO | WO 2013/016435 A1 | 1/2013 |
| WO | WO 2013/072777 A2 | 5/2013 |
| WO | WO 2013/105099 A2 | 7/2013 |
| WO | WO 2013/109756 A2 | 7/2013 |
| WO | WO 2014/081892 A1 | 5/2014 |
| WO | WO 2014/139845 A1 | 9/2014 |
| WO | WO 2014/169266 A1 | 10/2014 |
| WO | WO 2014/178198 A1 | 11/2014 |
| WO | WO 2015/061365 A1 | 4/2015 |
| WO | WO 2015/134625 A1 | 9/2015 |
| WO | WO 2015/179324 A2 | 11/2015 |
| WO | WO 2015/179377 A1 | 11/2015 |
| WO | WO 2015/189354 A1 | 12/2015 |
| WO | WO 2016/010995 A1 | 1/2016 |
| WO | 2018/193603 A1 | 10/2018 |
| WO | WO 2018/178979 A1 | 10/2018 |

OTHER PUBLICATIONS

International Search Report and Written Opinion issued for Application No. PCT/EP2017/0696688 dated Nov. 27, 2017.
International Search Report of PCT/IE2011/000057, dated Feb. 3, 2012 (5 pages).
International Search Report of PCT/IE2012/000011, dated Oct. 10, 2012 (3 pages).
Office Action issued in U.S. Appl. No. 14/737,249 dated Apr. 10, 2018.
Office Action issued in U.S. Appl. No. 15/158,384 dated Jul. 20, 2018.
Partial European Search Report issued in Application 17204015.6 dated May 17, 2018.
U.S. Office Action issued in corresponding U.S. Appl. No. 15/158,384 dated Jun. 12, 2019.
Written Opinion and International Search Report, dated Jul. 27, 2011, from international Application No. PCT/IE2011/000026 (8 pages).
Extended European Search Report issued in corresponding European Patent Application No. 20 19 5533 dated Feb. 8, 2021.

* cited by examiner

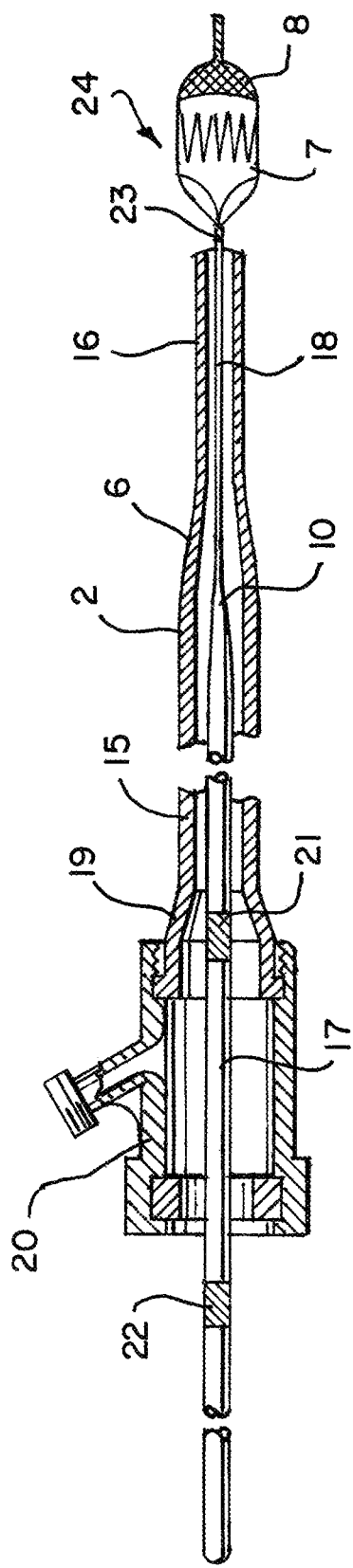
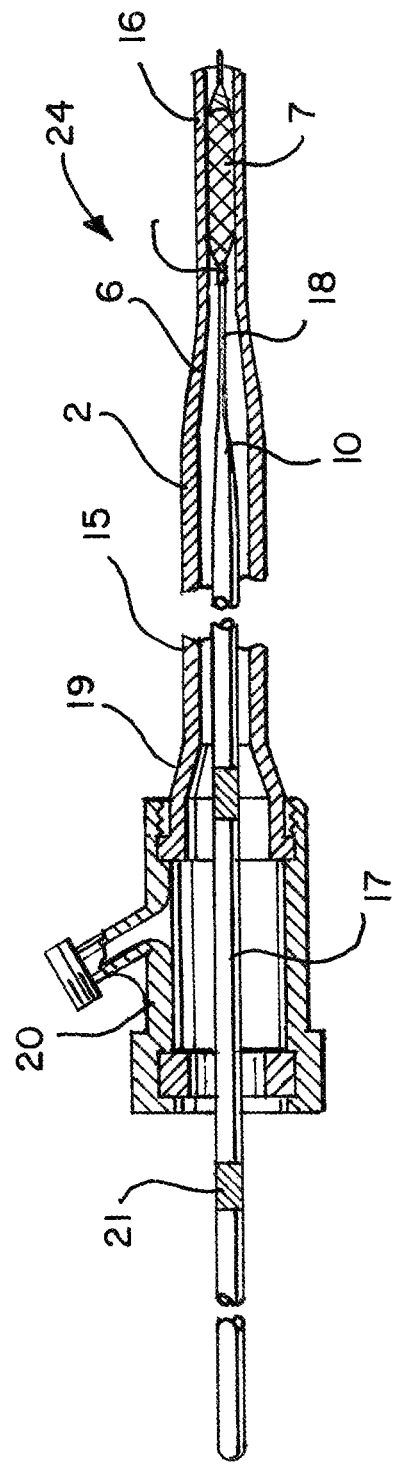

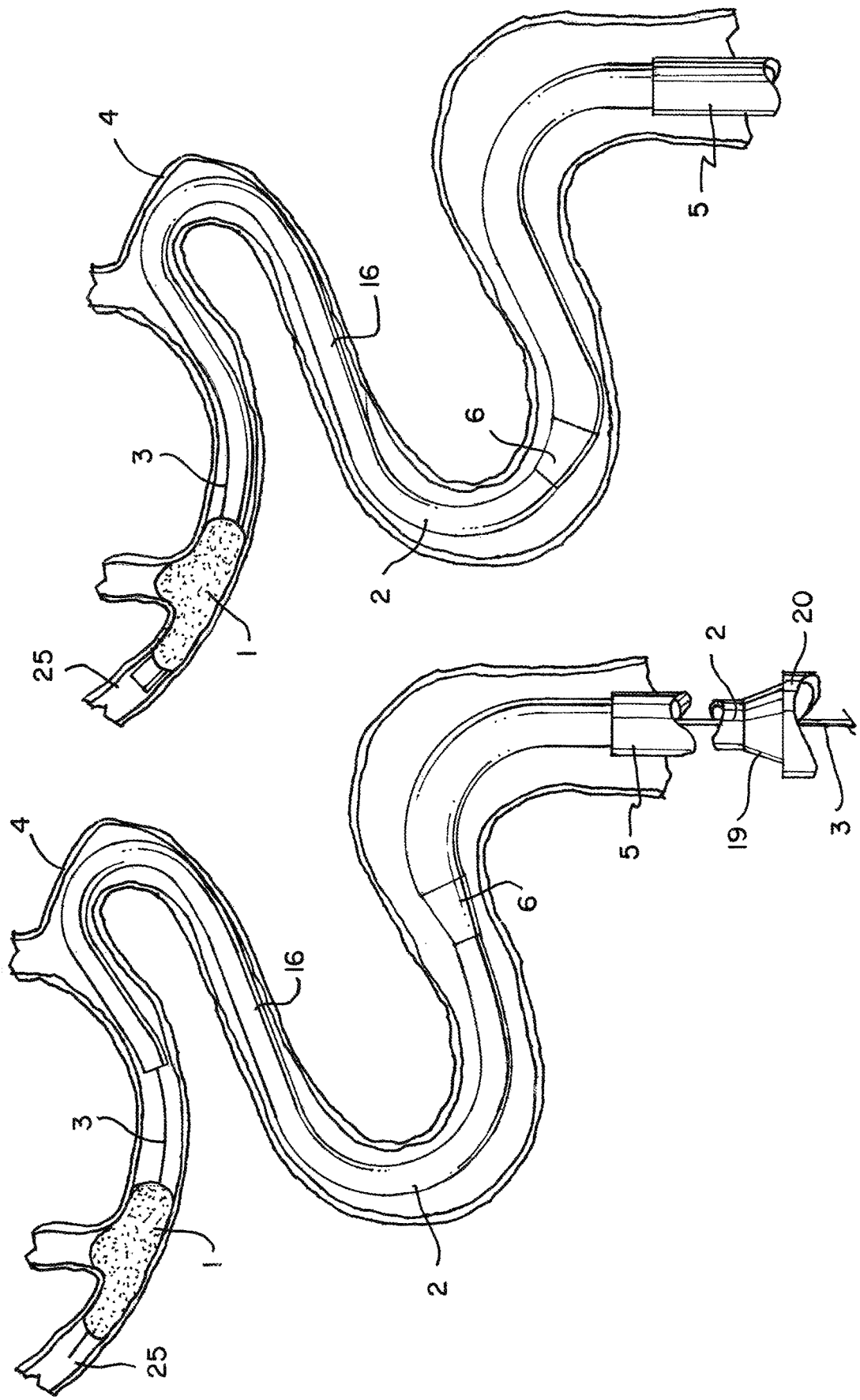

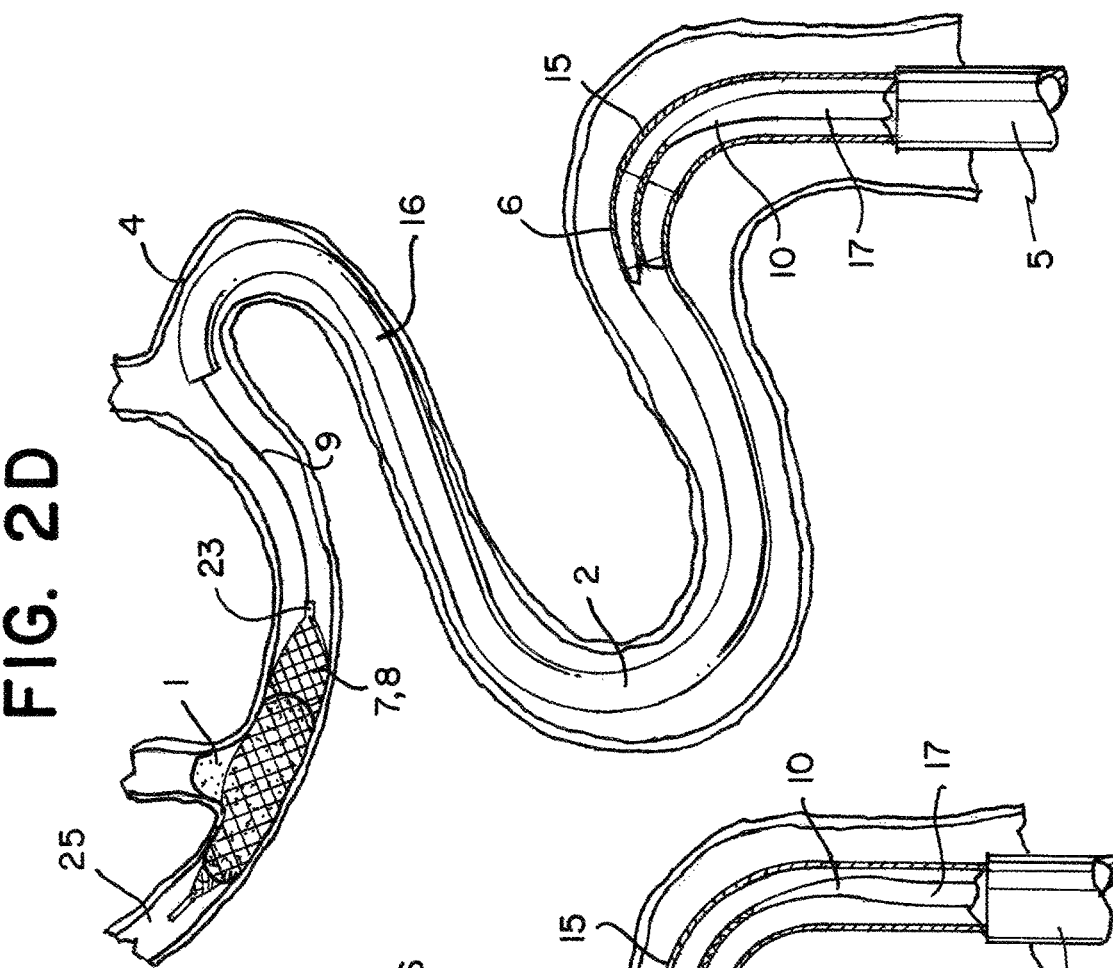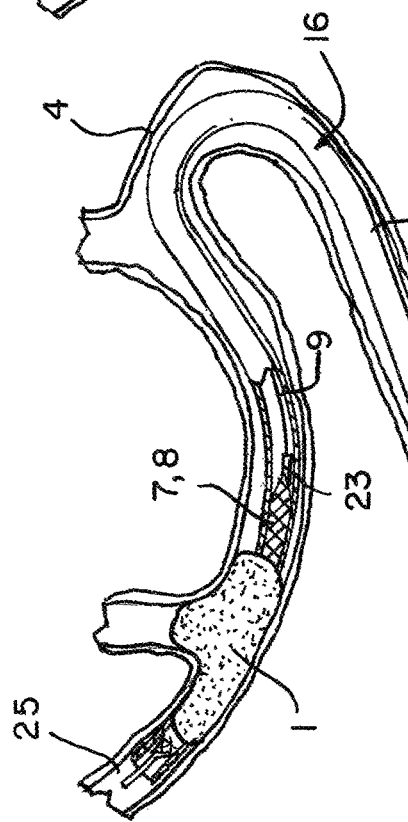

FIG. 3
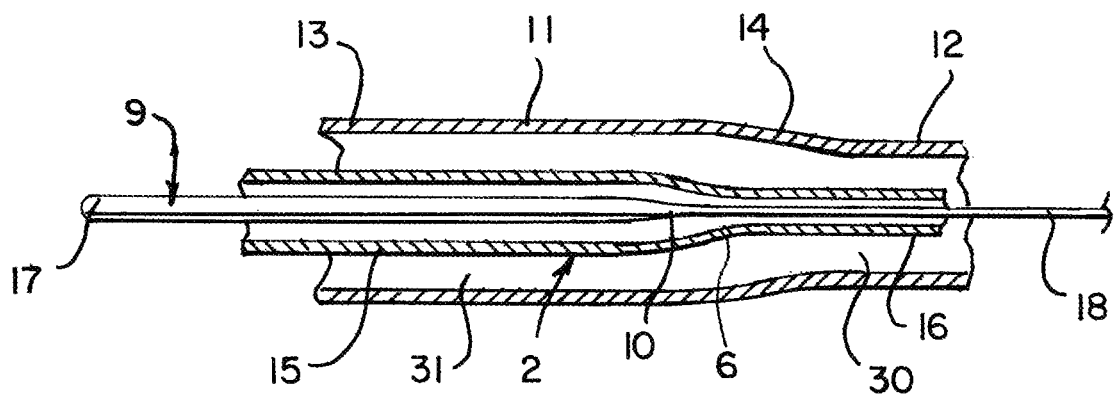
FIG. 4
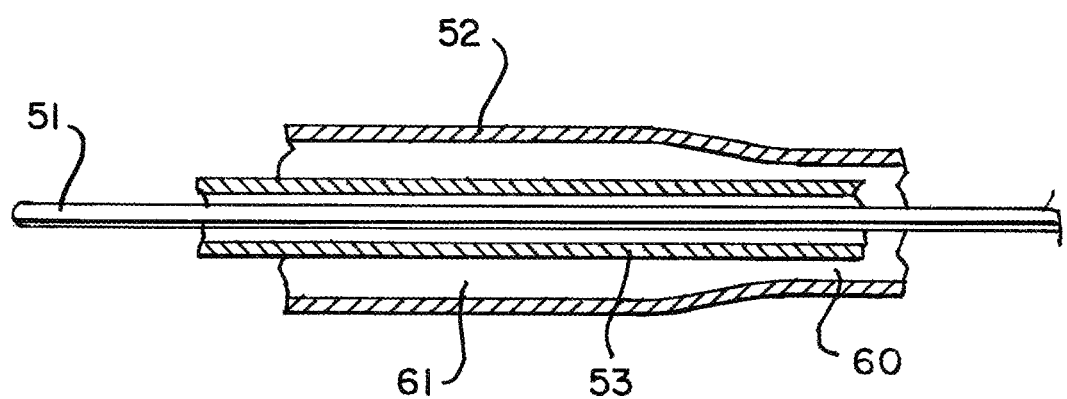
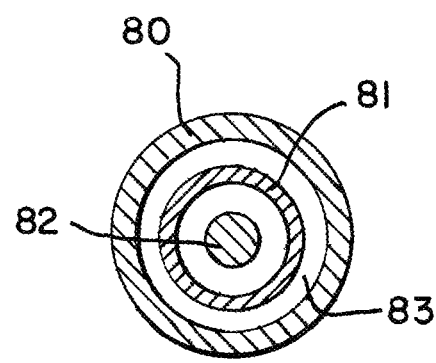
FIG. 5

SYSTEM FOR REMOVING A CLOT FROM A BLOOD VESSEL

CROSS REFERENCE TO RELATED APPLICATIONS

This application is a continuation of U.S. patent application Ser. No. 14/698,552, filed Apr. 28, 2015, which claims the benefit of U.S. Provisional Application No. 62/019,137, filed Jun. 30, 2014, the entirety of both which are incorporated herein by reference in their entirety.

INTRODUCTION

Acute ischemic stroke (AIS) is a worldwide problem for which until recently there have been only limited therapy options available for patients. One option for such patients is a lytic drug called tPa, which can be administered either intravenously or intra-arterially. More recently various mechanical thrombectomy and/or revascularisation devices have become available which aim to dislodge and remove the clot using mechanical means. These devices are typically advanced through a small catheter (called a microcatheter) to the site of the occlusive blood clot, whereupon they are deployed from this microcatheter and engaged with the clot. It would be advantageous for the patient and physician that this microcatheter be as flexible and small in diameter as possible, as these attributes enable the microcatheter to be advanced through tortuous vessel anatomies with ease without harming the vessel walls, and also enable the microcatheter to be advanced across the clot without pushing the clot further distally or dislodging a portion of the clot which might embolise another vessel. However it may be challenging for a mechanical thrombectomy and/or revascularisation device to pass through such a small diameter microcatheter. One particular challenge involves the ability to push the device through the microcatheter, especially around tortuous bends in distal anatomies. Many mechanical thrombectomy and/or revascularisation devices consist of a clot engaging element attached to the distal end of an elongate wire or shaft. This shaft extends exterior of the patient and is used by the physician to advance the device through the microcatheter to the site of the obstruction. This shaft therefore needs to be robust enough, and stiff enough, to be able to push the engaging element against significant resistance as it enters regions of tortuosity. However if the device is to be used with a very small diameter microcatheter (as is desirable) then the diameter of the shaft is limited to a size somewhat smaller than the inner diameter of this microcatheter. This trade-off between microcatheter profile and shaft profile means that conventional mechanical thrombectomy and/or revascularisation devices either a) are compatible with very small diameter microcatheters but suffer from having flimsy shafts which are easily damaged and cannot effectively transmit a push force to advance the device around significant tortuosity, or b) are fitted with sufficiently large diameter shafts to have good robustness and pushability but are not compatible with very small diameter microcatheters.

It is desirable for a Thrombectomy Device (TD) to have a very low delivery profile in order to cross an occlusive clot easily and without dislodging any clot material. Most TDs are delivered through a microcatheter, and it is the microcatheter (and typically an inner guidewire) that first cross the clot. After that the guidewire is removed and the TD is advanced through the microcatheter. Thus it is desirable that the TD be compatible with microcatheters that are as small as possible in diameter. A further advantage of a small diameter microcatheter is that increased space is available between the microcatheter and the inner surface of a guide catheter or intermediate catheter through which it passes. This increased space makes it easier to aspirate blood and clot from the site of occlusion through the guide or intermediate catheter, which is a method typically used in conjunction with use of a thrombectomy device. Some physicians choose to remove the microcatheter completely before aspirating in order to increase this space and reduce the resistance to flow through an intermediate catheter, particularly if a large diameter microcatheter and/or small diameter intermediate catheter is used. It would be desirable if such a step were not required.

It is generally necessary to have some clearance between the inner diameter of a catheter and the outer diameter of the shaft of a device that is passed through it. Without any clearance the shaft would not move freely through the catheter and would be very difficult to advance. The clearance required depends on both the internal diameter of the catheter (its lumen) and the degree or tortuosity of the vasculature in which it is positioned. In relatively low levels of tortuosity a small clearance between shaft and catheter lumen may be perfectly adequate, but in higher levels of tortuosity greater clearance may be required to permit free movement. For example, in the case of a neurovascular thrombectomy system used in middle cerebral artery via femoral access: a clearance of less than 0.003" (ie 0.0025", 0.002" or even less than 0.002") may be adequate for the proximal section of the system which sits proximal of the patients aortic arch take off, while a clearance of 0.003" or more may be required to permit free movement of the thrombectomy device shaft through the microcatheter in the section of the system distal of the common carotid artery.

Many TDs today are compatible with microcatheters with an inner lumen of approximately 0.021" and an outer diameter of 0.025" to 0.034" or more. These TDs can therefore be mounted on shafts that have an outer diameter of up to approximately 0.018" (to comfortably fit in the 0.021" lumen). Some TDs are compatible with smaller microcatheters which have a lumen of approximately 0.016" to 0.17" and an outer diameter as low as approximately 0.020". These lower profile catheters may be more easily advanced into tortuous distal vessels and may cross clots more easily due to their lower profile. However a TD that is designed to fit through one of these catheters must have a shaft diameter of approximately 0.014" or less. The bending stiffness of a 0.014" shaft is 63% lower than that of a 0.018" shaft of the same material, because the bending stiffness is proportional to the fourth power of the shaft diameter. Therefore the pushability of the 0.014" shaft is also much less than that of the 0.018" shaft. Thus a 0.014" shaft would need to have a much higher modulus of elasticity than an 0.018" shaft in order to deliver a similar level of "pushability". However it is desirable that these shafts are made from a superelastic or shape memory material such as nitinol so that they retain their shape and do not become kinked or deformed after use, as they may need to be reused for additional clot retrieval passes if the first is not successful. One way to attain a higher modulus and hence recover some pushability would be to change shaft material to stainless steel or other relatively high modulus material. However this means compromising on the kink resistance and durability of the nitinol shaft. Thus there is a need for a solution to this undesirable trade-off problem.

The solutions provided herein are applicable not just to AIS, but also to the removal of obstructions from vessels throughout the body, such as peripheral arteries and veins, coronary vessels and pulmonary vessels where embolism can be a serious problem

STATEMENTS OF INVENTION

According to the invention there is provided a system for removing obstructions from a blood vessel, the system comprising a clot retrieval device and a catheter. The clot retrieval device comprises a clot engaging element and an elongate shaft; the clot engaging element having a first collapsed delivery configuration and a second expanded deployed configuration. The elongate shaft has a shaft proximal section, a shaft distal section and a shaft intermediate section between the shaft distal and proximal sections. The clot engaging element being attached to the shaft distal section of the elongate shaft. The catheter has a catheter proximal section, a catheter distal section, and a catheter intermediate section between the proximal and distal sections. The catheter proximal section has an inner proximal lumen and an outer proximal diameter, the catheter distal section having an inner distal lumen and an outer distal diameter.

In one embodiment the maximum diameter of the shaft proximal section is greater than the inner distal lumen of the catheter distal section.

In one embodiment the maximum diameter of the shaft proximal section is less than 0.003" smaller than the inner distal lumen of the catheter distal section.

In one embodiment the maximum diameter of the shaft proximal section is less than 0.002" smaller than the inner distal lumen of the catheter distal section.

In one embodiment the maximum diameter of the shaft proximal section is greater than the maximum diameter of the shaft distal section.

In one case the inner proximal lumen of the catheter is larger than the inner distal lumen of the catheter.

In some cases the outer proximal diameter of the catheter is larger than the outer distal diameter of the catheter.

In one embodiment the outer proximal diameter of the catheter is equal to the outer distal diameter of the catheter (see, e.g., FIG. 6).

The clot engaging element may be self-expandable. The clot engaging element may comprise a self-expanding nitinol body.

The invention also provides a method for removing obstructions from a blood vessel comprising:—
  providing a clot retrieval device and a catheter system according to the invention;
  positioning a guide catheter or sheath proximal of an obstruction in a blood vessel;
  advancing a guidewire towards the obstruction;
  advancing the catheter over the guidewire;
  removing the guidewire;
  advancing the elongate clot retrieval shaft through the catheter with the clot retrieval element in the collapsed delivery configuration;
  advancing the catheter and the shaft through the obstruction;
  deploying the clot engaging element in the obstruction;
  retracting the catheter to a position proximal of the clot retrieval element; and
  retrieving the clot retrieval element and the clot captured by the retrieval element.

BRIEF DESCRIPTION OF THE DRAWINGS

The invention will be more clearly understood from the following description of an embodiment thereof, given by way of example only, with reference to the accompanying drawings, in which:
FIG. 1a is a cross sectional side view of a clot retrieval system according to the invention;
FIG. 1b is a cross sectional side view of a clot retrieval system according to the invention;
FIGS. 2a to 2e are views illustrating the clot retrieval system in use.
FIG. 3 is a cross sectional side view of a portion of a clot retrieval system according to the invention.
FIG. 4 is a cross sectional side view of a portion of a conventional clot retrieval system.
FIG. 5 is a cross sectional view through FIGS. 3 and 4.

DETAILED DESCRIPTION

Figure 2E:
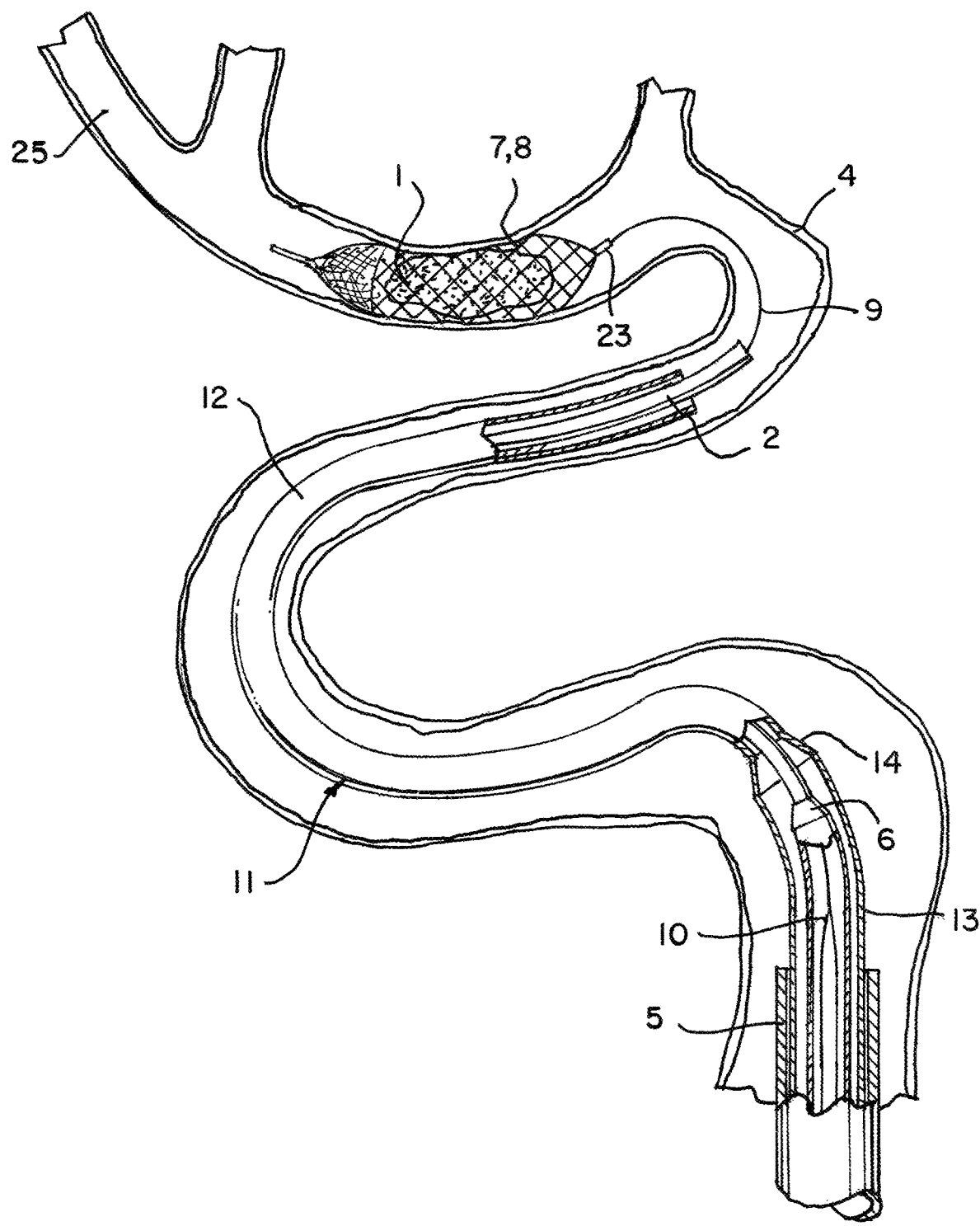
Figure 6:
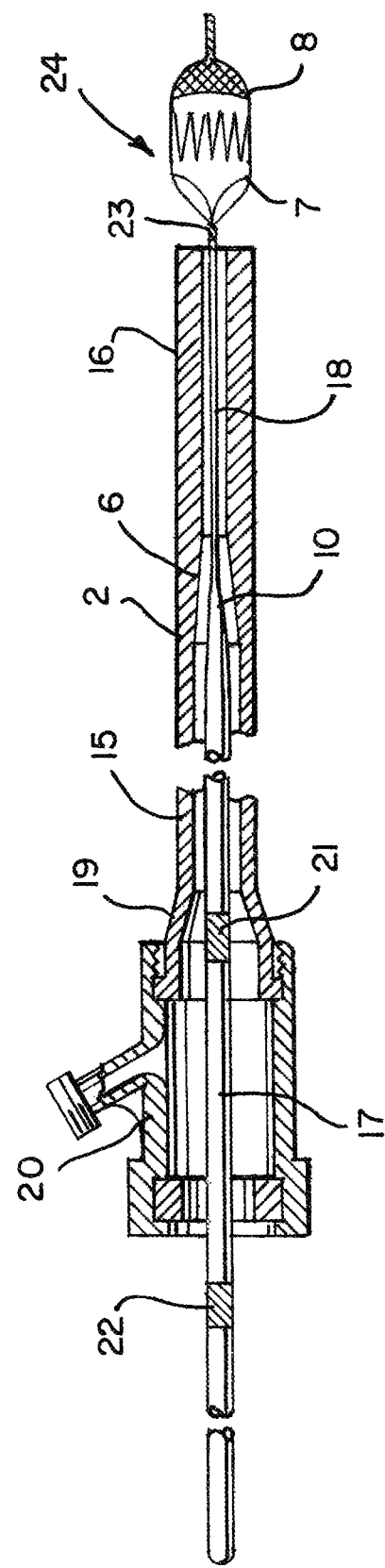
FIG. 6 is a cross sectional side view of a clot retrieval system according to the invention.

Referring to FIGS. 1a and 1b of the drawings there is illustrated a system 24 for removing obstructions such as clot from a blood vessel, the system comprising a clot retrieval device 8 having a clot retrieval element 7 mounted at the distal end of an elongate shaft 9 and a catheter 2 which in this case is a microcatheter which is used to deliver the clot retrieval element 7 in a collapsed delivery configuration across a clot. The clot retrieval element 7 is deployed from the catheter 2 into an expanded deployed configuration for clot retrieval. FIG. 1a shows the system with the clot retrieval element 7 in the deployed expanded condition. FIG. 1b shows the system with the clot retrieval element 7 collapsed within the distal portion 16 of the microcatheter 2, just prior to deployment.

The catheter 2 comprises a catheter proximal section 15, a catheter distal section 16, and a catheter intermediate section 6 between the proximal and distal section. The catheter distal section 16 has an inner distal lumen and an outer distal diameter. The catheter proximal section 15 has an inner proximal lumen and an outer proximal diameter. The catheter comprises a hub 19 at its proximal end to which is typically attached a rotating haemostasis valve (RHV) 20, through which fluids may be injected or aspirated and which incorporates a seal to prevent the ingress of air and loss of blood or other fluids.

The shaft 9 of the clot retrieval device comprises a shaft proximal section 17, a shaft distal section 18 and a shaft intermediate section 10 between the shaft distal and proximal sections. The clot engaging element 7 is attached to the shaft distal section 18 of the shaft 9 at connection point 23 and may be self-expandable. For example, the clot engaging element may be formed from or comprise a self-expanding Nitinol body. Indicator bands 21 and 22 may be provided on the proximal shaft 17, to inform the user of the proximity of the clot retrieval element 7 to the distal end of the microcatheter 2.

The catheter 2 has a stepped diameter. The distal section 16 of the catheter 2 has a low profile (for example 0.16" inner diameter (ID)/0.020" outer diameter (OD)) for excellent flexibility and clot crossing capability. The proximal section 15 of the catheter 2 has a larger inner (and outer) diameter to accommodate a robust and pushable proximal shaft 17 of the clot retrieval device.

In one embodiment of the invention the maximum diameter of the shaft proximal section 17 is larger than the inner distal lumen of the catheter distal section 16. In another similar embodiment the shaft proximal section 17 is very slightly smaller than the inner distal lumen of the catheter distal section 16, so that the catheter can be completely withdrawn over the shaft when in a relatively straight configuration, while still benefiting from a robust large diameter shaft.

As the catheter 2 is not typically withdrawn more than a short distance during use, the shaft proximal section 17 may be even larger than the internal diameter (ID) of the distal section 16 of the catheter 2. In some cases the shaft proximal section 17 is only slightly smaller (i.e. 0.003" or less smaller or 0.002" or less smaller) than the ID of the distal section 16 of the catheter 2—for example the distal section of the catheter may have a lumen of 0.0175", and the shaft proximal section may have an OD of 0.016". This diameter difference allows the microcatheter 2 to be completely withdrawn over the device shaft 9 if desired, provided that the larger diameter proximal portion of the device shaft 17 is not positioned in a region of significant tortuosity.

FIGS. 2a to 2e show a method of use of the clot retrieval system 24 of this invention. FIG. 2a shows a clot 1 lodged in vasculature 25 causing an obstruction to the flow of blood. A large diameter guide catheter or sheath 5 is positioned in a vessel proximal of the obstructive clot. A microcatheter 2 is advanced through the guide or sheath 5 towards the clot 1 with the aid of guidewire 3. A region of tortuousity exists between the distal end of guide or sheath 5 and the clot 1, comprising at least one tight bend 4. Such tortuosity may comprise bends if radii less than 1 0mm and in some cases less than 5 mm, and may also comprise "figure of 8" loops and compound curves are very difficult to navigate through without a highly flexible microcatheter. In addition the clot itself may be difficult to cross. Hence it is advantageous to provide a flexible and low profile distal segment 16 in a microcatheter such as that of this invention, which also comprises a supportive and robust proximal section 15 with which to advance the catheter through the challenging region of tortuousity and across the clot. The length of the distal low profile, flexible section 16 is at least long enough such that only this low profile section reaches the clot 1, and most preferably such that only this low profile section reaches the region of tortuousity distal of the guide or sheath 5. For treatment of AIS this catheter section is therefore ideally at least 5 cm in length and is most preferably between 10 cm and 30 cm in length. In other embodiments the distal section 16 may extend to as much as 100 cm or more, which will provide the benefit of increased luminal space for aspiration within an intermediate catheter (if used), but at the cost of some pushability performance of the microcatheter.

Once the microcatheter has been successfully advanced across the clot 1, the guidewire 3 is removed as shown in FIG. 2b, so that clot retrieval device 8 can be advanced through the lumen of the microcatheter 2 towards the target clot as shown in FIG. 2c. The microcatheter 2 is then retracted to allow the clot retrieval element 7 to expand within and grip the clot 1 as shown in FIG. 2d. The distal shaft section 18 ideally has a longer length than the distal microcatheter section 16, so that the microcatheter can be retracted to a position proximal of the clot retrieval element as shown in FIG. 2d. As with the microcatheter, the larger diameter and stiffer proximal section 17 of the clot retrieval device shaft provides the shaft with greater pushability than would be the case with a lower profile shaft, enabling the user to advance the device more easily through the challenging region of tortuousity distal of the guide or sheath 5, and around tight bend 4.

Once the clot retrieval element 7 has been deployed within the clot it may be left for a few minutes to expand and embed within the clot or it may be withdrawn immediately according to the physicians preference. In either case the clot and retrieval element may be withdrawn directly back into guide or sheath 5, or an intermediate catheter 11 may be used in a "tri-axial" set-up as shown in FIG. 2e. Aspiration though the guide/sheath and/or intermediate catheter is typically used to assist in creating a reversal of blood flow and safely retrieving back the clot and any clot fragments that may be liberated. This aspiration can be applied by means of a syringe or vacuum pump connected to the proximal end of the intermediate catheter. If this aspiration is applied through an intermediate catheter the space within the lumen of this catheter has a significant impact on the flow rate that can be created for a given aspiration force. As a maximum of 1 atmosphere vacuum can be created by a syringe or vacuum pump the luminal space is a critical factor in optimising the effect of this vacuum on flow rate.

FIG. 3 shows a simplified view of a cross section through a system incorporating an intermediate catheter 11 as shown in use in FIG. 2e. The intermediate catheter 11 may have a stepped profile as shown with a large lumen in proximal section 13 than in distal section 12, or in other embodiments may have a constant inner diameter. The distal luminal space 30 and proximal luminal space 31 are the areas between the outer surface of the microcatheter 2 and the inner surface of the intermediate catheter 11 through the aspiration force is applied. The effective flow rate through such a system is a function of the cross-sectional areas and lengths of spaces 30 and 31, and the viscosity of the fluid in question (which is blood). Thus it is advantageous to maximise the cross-sectional areas and minimize the lengths of spaces 30 and 31.

FIG. 4 shows a simplified view of a cross section through a conventional thrombectomy system incorporating an intermediate catheter 52, a microcatheter 53 with a continuous non-stepped inner lumen, and a clot retrieval device shaft 51. Comparing FIGS. 3 and 4 it can be seen that the system of this invention depicted in FIG. 3 has a much larger distal luminal space 30 than the distal luminal space 60 provided by the conventional system of FIG. 4. This provides a major advantage in that with the system of this invention aspiration can be very effectively applied without the need to remove the microcatheter from the patient. Removal of the microcatheter can be both time consuming and difficult as thrombectomy device shafts are not typically long enough to permit this to be done without the addition of an extension piece to the shaft.

FIG. 5 shows a cross-sectional view representative of that through the systems of both FIG. 3 and FIG. 4, where clot retrieval shaft 82 lies within microcatheter 81, which in turn sits within the lumen of intermediate catheter 80, leaving luminal space 83 between the two for aspiration.

The invention enables clot retrieval devices with robust and pushable shafts to be used in conjunction with flexible, small diameter microcatheters, and enables aspiration forces to be effectively transmitted through an intermediate or guide catheter without the need for removing the microcatheter.

The clot retrieval device may, for example, be of the type described in our US2013/0345739A or US2014/0371779A the entire contents of which are incorporated herein by reference.

The invention is not limited to the embodiment hereinbefore described, with reference to the accompanying drawings, which may be varied in construction and detail.

What is claimed is:

1. A system for removing an obstruction from a blood vessel, the system comprising:
 a catheter comprising:
  a proximal section with a proximal section lumen diameter,
  a distal section with a distal section lumen diameter less than the proximal section lumen diameter,
  an intermediate section extended between proximal and distal sections; and
 a clot retrieval device comprising:
  a clot engaging element having a first collapsed delivery configuration and a second expanded deployed configuration; and
  a shaft being advanceable through the lumen of the catheter the obstruction of the blood vessel, the shaft comprising:
   a shaft proximal section;
   a shaft distal section attached to the clot engaging element and configured to cross the obstruction, a diameter of the shaft proximal section being greater than a diameter of the shaft distal section thereby inhibiting the shaft proximal section from distally advancing through the catheter distal section; and
   a shaft intermediate section distal of the shaft proximal section and extended between the shaft distal section and the shaft proximal section; and
  wherein the intermediate and distal sections of the catheter and shaft are advanceable through the blood vessel towards the clot;
  wherein the shaft proximal section is stiffer than the shaft distal section.

2. The system as claimed in claim 1, wherein a distal luminal space being maximized between the shaft distal section and the catheter distal section.

3. The system as claimed in claim 1, wherein the shaft proximal section diameter is 0.003" or less smaller than the inner diameter of the catheter distal section.

4. The system as claimed in claim 1, wherein an outer diameter of the catheter proximal section is larger than an outer diameter of the catheter distal section.

5. The system as claimed in claim 1, wherein the catheter proximal section is substantially robust and the catheter distal section is substantially flexible.

6. The system as claimed in claim 1, wherein the shaft further comprises a radiopaque indicator.

7. A system, comprising:
 a shaft having a proximal section with a proximal section diameter and a distal section with a distal section diameter, wherein the distal section diameter is smaller than the proximal section diameter;
 an expandable clot engaging element attached to the distal section of the shaft;
 a first catheter having a first catheter proximal section and a first catheter distal section, wherein the first catheter comprises a lumen extending therethrough, wherein the shaft is distally advanceable within the first catheter and the first catheter proximal section comprises a proximal section lumen diameter larger than a distal section lumen diameter; and
 a second catheter, the first catheter being advanceable within a lumen of the second catheter;
 wherein the proximal section diameter of the shaft is greater than the distal section lumen diameter of the first catheter distal section thereby inhibiting the shaft proximal section from distally advancing through the catheter distal section;
 wherein the second catheter comprises a second catheter proximal section and a second catheter distal section, wherein an outer diameter of the second catheter proximal section is larger than an outer diameter of the second catheter distal section.

8. The system as claimed in claim 7, wherein an outer diameter of the first catheter proximal section is larger than an outer diameter of the first catheter distal section.

9. The system as claimed in claim 7, wherein the second catheter has a lumen extending therethrough, wherein the lumen of the second catheter has a diameter larger than an outer diameter of the first catheter proximal section.

10. The system as claimed in claim 7, wherein the shaft further comprises a radiopaque indicator.

11. A method, comprising:
 advancing a clot engagement element, by distally advancing a shaft through a catheter, wherein the shaft comprises: a shaft proximal section, a shaft distal section with a diameter less than the shaft proximal section, the shaft distal section being attached to the clot engagement element, and a shaft intermediate section between the shaft proximal and distal sections,
 extending the catheter across an obstruction in a blood vessel, wherein the catheter comprises: a catheter proximal section, a catheter distal section with a diameter less than the catheter proximal section, a catheter intermediate section between the catheter proximal and distal sections;
 retracting the catheter so as to expand and deploy the clot engagement element distal of the catheter within the obstruction;
 retrieving the clot engagement element and the obstruction from the blood vessel;
 advancing a guidewire across the obstruction and through the catheter; and,
 removing the guidewire from the catheter after advancing the catheter.

12. The method as claimed in claim 11, wherein the shaft intermediate section is advanceable through the catheter proximal section and the intermediate and distal sections of the catheter and shaft being are advanceable through the blood vessel towards the obstruction.

13. The method as claimed in claim 11, further comprising: inhibiting the shaft proximal section from distally advancing through the catheter distal section by preventing the proximal section diameter of the shaft from passing through the distal section lumen of the catheter distal section.

14. The method as claimed in claim 11, further comprising: visualizing the shaft through a radiopaque indicator of the shaft.

15. The method as claimed in claim 11, further comprising:
 maximizing a distal luminal space defined between the shaft distal section and the catheter distal section.

16. The method as claimed in claim 11, wherein the catheter is a first catheter, the method further comprising:
 advancing a second catheter to a first location proximal of the obstruction, and
 advancing a guide catheter to a second location proximal of the obstruction,
 wherein the retrieving comprises withdrawing the clot engaging element into a lumen of at least one of the second catheter or the guide catheter.

17. The method as claimed in claim 16, wherein the second catheter comprises a second catheter proximal section that extends to a second catheter distal section, wherein an outer diameter of the second catheter proximal section is larger than an outer diameter of the second catheter distal section so that the second catheter distal section is advanceable at least up to and through the first catheter proximal section.

* * * * *